United States Patent [19]
Horn et al.

[11] Patent Number: 4,931,270
[45] Date of Patent: Jun. 5, 1990

[54] METHOD FOR DETECTING DOPAMINERGIC DISEASES USING FLUORINE-18 RADIOLABELLED $D_2$ DOPAMINE RECEPTOR LIGANDS

[75] Inventors: Alan S. Horn, Groningen, Netherlands; Paul A. Jerabek, Long Beach; James V. Peck, Costa Mesa, both of Calif.

[73] Assignee: Nelson Research & Development, Irvine, Calif.

[21] Appl. No.: 216,405

[22] Filed: Jul. 7, 1988

[51] Int. Cl.$^5$ .............................................. A61K 49/02
[52] U.S. Cl. ......................................... 424/1.1; 424/9
[58] Field of Search ..................... 424/9, 1.1

[56] References Cited
PUBLICATIONS

Ames, et al, "The Synthesis of Alkoxy-1,2,3,4-tetrahydronaphthalene Derivates. Part I. 2-Amino, Alkylamino-, and Dialkylamino-derivatives," *J. Chem. Soc.*, 2636 (1986).

Andreasen, et al., "Brain Imaging: Application in Psychiatry", *Science* 239, 1381-1388 (1988).

Arnett, et al., "Improved Delineation of Human Dopamine Receptors Using [$^{18}$F]-N-Methylspiroperidol and PET", *J. Nucl. Med.* 27(12) 1878-1882 (1986).

Berridge, "Chemistry of Fluorine-18 Radiopharmaceuticals", *Appl. Radiat. Isot.* 37(8) 685-693 (1986).

Chi et al, "A Rapid and Efficient Method for Fluoroalkylation of Amines and Amides. Development of a Method Suitable for Incorporation or the Short-Lived Positron Emitting Radionuclide Fluorine-18", *J. Org. Chem.* 52 658-664 (1987).

Chi, et al, "Synthesis of No-Carrier-Added N-([$^{18}$F]-Fluoroalkyl)Spiperone Derivatives", *Appl. Radiat. Isot.* 37(12) 1173-1180 (1986).

Crowe, et al., "Studies in the Thiophene Series, VI. Azlactones and Rhodanines Prepared from 2-Thenaldehyde and Some Substituted 2-Thenaldehydes", *J. Org. Chem* 15, 81 (1950).

Daly, et al, "Structure-Activity Relationship for $N^6$-Substituted Adenosines at a Brain $A_1$-Adenosine Receptor with a Comparison to an $A_2$-Adenosine Receptor Regulating Coronary Blood Flow", *Biochem. Pharmac.* 35(15) 2467-2481 (1986).

Farde, et al, "Quantitative Analysis of $D_2$ Dopamine Receptor Binding in the Living Human Brain by PET", *Science* 231, 258-261 (1986).

Hagglund, et al, "Dopamine Receptor Properties in Parkinson's Disease and Huntington's Chorea Evaluated by Positron Emission Tomography Using $^{11}$C-N-Methyl-Spiperone", *Acta Neurol Scand* 75:87-94 (1987).

Hoffmann, "Aliphatic Fluorides, II. 1-Halogen Fluoroalkanes", *J. Org. Chem.* 15, 425 (1950).

Mulder, et al, "Kinetic and Pharmacological Profiles of the In Vitro Binding of the Potent Dopamine Agonist [$^3$H]N,N-Dipropyl-5, 6-Dihydroxy-2-Aminotetralin to Rat Straital Membranes", *Eur. J. Pharmac.* 112 73-79 (1985).

Phelps, et al, "Positron Emission Tomography: Human Brain Function and Biochemistry", *Science* 228 (4701) 799-809 (1985).

Raichle, "Positron Emission Tomography", *Ann. Rev. Neurosci.* 6:249-267 (1983).

Seeman, "Brain Dopamine Receptors", *Pharmacol. Rev.* 32(3) 229-313 (1980).

Seeman, et al, "Dopamine $D_2$ Receptor Binding Sites for Agonists, A Tetrahedral Model", *Molec. Pharmacol.* 28:391-399 (1985).

Van Der Werf, et al, "Synthesis and In Vivo Distribution in Rat Brain of $^{11}$C-Labelled N-Alkylated ADTN Derivatives", *Int. J. Appl. Radit. Isot.* 35(5) 377-381 (1984).

Wong, et al, "Positron Emission Tomography Reveals Elevated $D_2$ Dopamine Receptors in Drug-Naive Schizophrenics", *Science* 234, 1558-1663 (1986).

*Primary Examiner*—John S. Maples
*Attorney, Agent, or Firm*—Robert J. Baran; June M. Bostich

[57] ABSTRACT

Abnormalitites in the distribution of a dopamine $D_2$ receptors in humans and other mammals are detected by
(1) administering to a human or other mammal an amount of a $^{18}$F-radiolabelled compound sufficient to be detected by a positron emission sensitive means for imaging, said compound having affinity for said receptors selected from the group consisting of optically active or racemic compounds represented by the general formula:

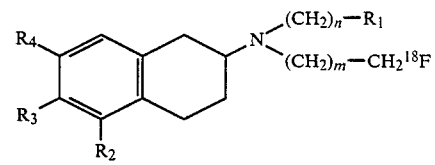

(2) forming at least one image showing the distribution of the radiolabelled compound within the human or other mammal using a positron emission-sensitive means for imaging; and
(3) determining normality of the concentrations or distribution by comparing the image with an image showing the normal concentrations and distribution of the receptors in humans or mammals of the same species wherein R1-R4, n and m- are as set forth in the specification.

22 Claims, No Drawings

METHOD FOR DETECTING DOPAMINERGIC DISEASES USING FLUORINE-18 RADIOLABELLED D$_2$ DOPAMINE RECEPTOR LIGANDS

FIELD OF THE INVENTION

This invention relates to radiolabelled compounds with affinity for D$_2$ dopamine receptor sites in humans and other mammals. More particularly, this invention relates to $^{18}$F-containing D$_2$ dopamine agonist receptor ligands and to a process for in vivo detection of dopamine D$_2$ receptor function abnormalities in the human brain.

BACKGROUND OF THE ART

The study of human brain function and its alterations with disease is founded on our increasing understanding of the biochemical nature of the brain. The earliest and most specific changes occurring in diseases of the brain are those that disturb its underlying biochemical processes.

In the past, information about the structure and processes of the human brain were dependent upon biopsies or chemical assays of blood, cerebrospinal fluid, or urine. More recently, development of positron emission tomography (PET) has furthered our understanding of the structure, organization and chemical basis of both normal and diseased cerebral function.

In positron emission tomography, biologically active substrates can be radiolabelled by replacing natural elements of the biochemical constituents of the body with the corresponding radioisotopes. For example, natural isotopes of carbon, nitrogen, and oxygen in biological molecules are replaced with the corresponding radio isotopes carbon-11, nitrogen-13, or oxygen-15. In addition, fluoride-18 can be used in biological molecules. These radioisotopes have short half-lives ranging between 2 minutes for $^{15}$O and 110 minutes for $^{18}$F, and they all decay by emission of positrons. Positrons, which are positively charged electrons, travel only a few millimeters in living tissue before encountering an electron, resulting in an event that annihilates both particles. The mass of the two particles is converted into two photons traveling in directions approximately 180 degrees from each other with sufficient energy (511,000 electron volts each) to penetrate the bony structures of the head and to be detected externally, for example, by special equipment known as a tomograph.

The tomograph consists of an array of radiation detectors placed circumferentially around the body of the subject. The radiation detectors are connected to a coincidence circuit that records an event from the tissue only if both detectors sense an anihilation photon simultaneously.

The events registered by the detectors are fed into a fast computer which reconstructs images based on the distribution and frequency of radioactive events within the subject. The computer's reconstruction in a section of the imaged object is a quantitative representation of the spatial distribution of the radionuclide used. Detection systems currently employed in PET have a resolution of approximately 5-7 millimeters in the plane of the tomographic section.

Using quantitative tracer methods, PET allows measurement of the changes with time of tissue concentrations of the labelled compound throughout the brain. Therefore a quantitative, non-invasive in vivo technique is provided for tracing such biological processes as hemodynamics, transport phenomena, and neurotransmitter localization via tracer kinetic mathematical models.

Quantitative PET methods have been developed for use in the study of dopaminergic receptor systems, as well as for opiate and benzodiazepine systems. These types of PET studies are transformed into measurements of processes such as receptor affinity and density, neurotransmitter concentration and turnover, ligand off and on rates, and diffusion rates using kinetic and biochemical models.

Studies of the dopaminergic neurotransmitter system have linked it to Huntington's and Parkinsons' diseases as well as to schizophrenia. For instance, the antipsychotic action of neuroleptic drugs has been correlated with blockade of D$_2$ dopamine receptors. Amphetamines, which elevate synaptic dopamine levels, have been found to induce psychotic states resembling schizophrenia and to exacerbate symptoms of schizophrenic patients.

Increased numbers of D$_2$ dopamine receptors have been detected in the brains of diagnosed schizophrenic patients in post mortem studies. In some studies these increases were attributed to prior treatment of the patients with neuroleptics, while in other studies increased D$_2$ sites were found in vivo in drug-free schizophrenic patients. Wong, D. F., et al., "Positron Emission Tomography Reveals Elevated D$_2$ Dopamine Receptors in Drug-Naive Schizophrenics," Science. 24, pp. 1558–1562. Therefore, interpretation of increased numbers of D2 receptors in brain tissue remains controversial. An in vivo PET study of D$_2$ dopamine receptor levels comparing two groups of schizophrenic patients—one previously treated with neuroleptics and one group never treated with neuroleptics —has been used to estimate caudate D$_2$ dopamine receptor densities. Radiolabelled 3-N-[$^{11}$C]methyl-spiperone (half life of $^{11}$C is 20 minutes) was used to quantitate neurotransmitter receptor density and affinity in the brains of living subjects. Other studies have used [$^{11}$C]chlorpromazine, [$^{11}$C]raclopride, [$^{76}$Br]spiperone, [$^{18}$F]spiperone, [$^{18}$F]n-methylspiperone, 3-(2'-[$^{18}$F] fluoroethyl) spiperone, and N-(3-[$^{18}$F]fluoropropyl) spiperone. These studies indicate that a dopamine receptor abnormality, specifically an elevated level of D$_2$ dopamine receptors, is characteristic of untreated schizophrenic patients. See Arnett, et al., "Improved Delineation of Human Dopamine Receptors Using [$^{18}$F]-N-methylspiroperidol and PET," J. Nucl. Med. 27:1878–82, 1986.

There are several advantages of using $^{18}$F-labeled ligands for PET studies relative to $^{11}$C-labeled compounds. The radiolabelled biologically active substrates used in the D2 receptor studies all have relatively short half-lives, but the half-life of $^{18}$F is 110 minutes, while the half-life of $^{11}$C is only 20 minutes. Therefore, the time between production of the radiolabelled element in the cyclotron and introduction of the biologically active compound containing the radiolabelled element into the subject is about three half-lives for $^{11}$C, but only one half-life for $^{18}$F. Also, the time required after its introduction for the substrate to reach equilibrium in the human body should be no more than one additional half-life. The longer half-life of $^{18}$F provides greater time to reach equilibrium makes $^{18}$F doubly preferred over $^{11}$C for use in PET studies.

$^{18}$F-containing substrates are also preferred over $^{11}$C labelled substrates because of their higher specific activity, or radioactivity per unit mass and lower positron energy. A radiolabelled substrate having high specific activity is especially preferred for $D_2$ receptor studies because the $D_2$ receptor sites in the brain are normally in small concentration. As the specific activity of $^{18}$F-labelled substrates is usually five to six times higher than that of $^{11}$C labelled substrates, they are highly preferred for $D_2$ receptor PET studies.

However, the chemistry of $^{18}$F is known to be difficult. Fluorine gas reacts violently and indiscriminately with organic molecules. The reaction produces a mixture of products that is difficult to separate. Moreover, many reactions involving $^{18}$F are erratic and the yields are low. However, in recent years the knowledge of $^{18}$F chemistry and cyclotron target design has progressed to the point that $^{18}$F-containing radiopharmaceuticals of high purity and high specific activity can be produced.

Although several $^{18}$F radiolabelled dopaminergic compounds have been made with success, to date no dopamine agonists radiolabelled with positron-emitting radionuclides have been shown to retain selectivity of the ligand for dopamine $D_2$ receptor sites. See Van der Werf, "Synthesis and In Vivo Distribution in Rat Brain of $^{11}$C-Labelled N-Alkylated ADTN Derivatives," Int. S. Radiat. Isot, 35, 8, pp. 377–81, 1984.

In light of these developments, the need exists for new and better radiolabelled biologically active substrates having an affinity for binding to $D_2$ dopamine receptor sites and for a process of using such substrates to detect the occurrence of abnormalities in $D_2$ receptor functions. More particularly, the need exists for $^{18}$F-containing dopamine agonists having high specific activity and for the processes of making and using such substrates to determine abnormalities in the dopaminergic system.

SUMMARY OF THE INVENTION

A method is provided for detecting distribution of dopamine $D_2$ receptors in mammals wherein the method comprises (1) administering to a living human or other mammal an effective amount of a $^{18}$F- radiolabelled compound having affinity for said receptors selected from the group consisting of optically active or racemic compounds represented by the general formula

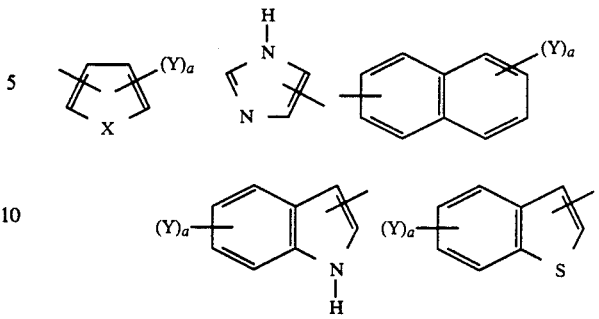

wherein $R_1$ is selected from the group consisting of organic radicals methyl, substituted or unsubstituted phenyls, pyridyl, hydroxyphenyl,

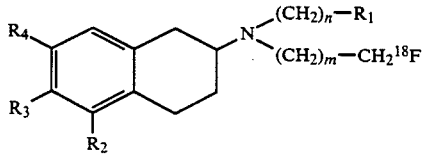

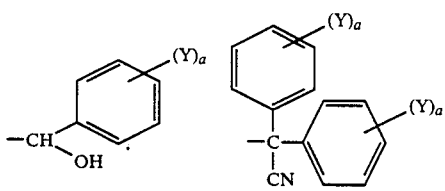

X is oxygen or sulfur, Y is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from zero to 3, $R_2$, $R_3$ and $R_4$ are each selected from the group consisting of H and OA, A is H or is selected from the group consisting of hydrocarbyl radicals,

and

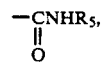

$R_5$ is selected from the group consisting of hydrocarbyl radicals; m is an integer between zero and 2; n is an integer between 1 and 3; and $R_6$ is an alkyl chain having between 1 and 3 carbon atoms with the provision that at least one of $R_2$, $R_3$ and $R_4$ is H, that at least one of $R_2$, $R_3$ and $R_4$ is not H, and that $R_2$ and $R_4$ are not both OA, except that when $R_1$ is meta-hydroxyphenyl, phenyl, or 2-thienyl, the compound is optically active and pharmaceutically acceptable salts thereof. Preferably, $R_2$ is hydroxyl.

Most preferably, $R_2$ is OA and A is H, m is 2, and the compound is the (−) isomer.

(2) forming an image showing distribution of the radio-labelled compound within the human or other mammal using positron emission sensitive means for imaging;

(3) determining from said distribution the concentration of dopamine D2 receptors in the human or other mammal; and (4) comparing said distribution with the average distribution of said receptors in a normal human or other mammal.

Preferably the method of determining abnormal levels of dopamine $D_2$ receptors is used to screen humans for schizophrenia, or parkinsonism, diseases thought to be characterized by abnormalities in the levels of dopamine $D_2$ receptors in the brain.

A DETAILED DESCRIPTION OF THE INVENTION

The radiolabelled $^{18}F$ dopamine agonist compounds of the invention having affinity for $D_2$ dopamine receptor sites in humans and other mammals are those selected from the group consisting of optically active or racemic compounds represented by the general formula:

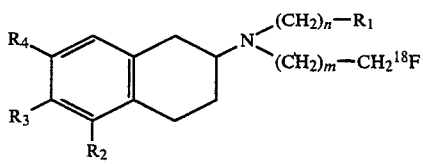

wherein $R_1$ is selected from the group consisting of organic radicals methyl, substituted or unsubstituted phenyls, pyridyl, hydroxyphenyl,

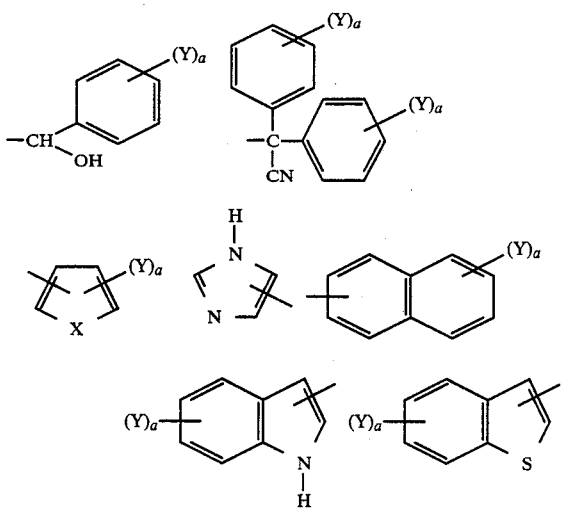

X is oxygen or sulfur, Y is selected from the group consisting of hydroxy, nitro, cyano, azido, amino, acylamino, carboxyamido, trifluoromethyl, sulfate, sulfonamido, halogen, hydrocarbyl and a hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from zero to 3, $R_2$, $R_3$ and $R_4$ are each selected from the group consisting of H and OA, A is H or is selected from the group consisting of hydrocarbyl radicals,

and

$R_5$ is selected from the group consisting of hydrocarbyl radicals; m is an integer between zero and 2; n is an integer between 1 and 3; and $R_6$ is an alkyl chain having between 1 and 3 carbon atoms with the provision that at least one of $R_2$, $R_3$ and $R_4$ is H, that at least one of $R_2$, $R_3$ and $R_4$ is not H, and that $R_2$ and $R_4$ are not both OA, except that when $R_1$ is meta-hydroxyphenyl, phenyl, or 2-thienyl, the compound is optically active and pharmaceutically acceptable salts thereof. Preferably, $R_2$ is oxygen.

Most preferably, $R_2$ is OA and A is H, m is 2, and the compound is the (−) isomer.

This invention is also intended to cover the stable fluorinated analogues of the above radiolabelled compounds. The fluorinated compounds in which the fluorine atom is the stable fluorine isotope, $^{19}F$, are also dopamine $D_2$ receptor agonists that possess an unusually high affinity for dopamine $D_2$ receptor sites, as is shown in the following example. Therefore the stable fluorinated agonist can be used for all of the usual purposes for which such agonists are used.

In one embodiment of the invention a radioisotope of the stable fluorinated compound is formed by replacing the stable fluorine atom with $^{18}F$. The methods for making both the intermediate and the radioactive compound are illustrated hereinbelow.

This invention further provides a method for detecting abnormal levels of dopamine $D_2$ receptors in the brains of humans and other mammals. In this method an $^{18}F$-radio-labelled species of the above fluorinated dopamine $D_2$ receptor agonist is administered to a human or other mammal having dopamine $D_2$ receptor sites so that the radio-labelled compound enters the brain via the bloodstream and interacts with $D_2$ receptor sites therein.

In research, the method and compounds of this invention are also useful for locating and monitoring the concentrations of dopamine $D_2$ receptor ligands at various sites in the body under the conditions of stress, shock, and the like. Hence, the methods herein may be used to identify heretofore unknown locations for dopamine $D_2$ receptor sites and physiological processes in various mammals and in humans.

A sufficient amount of the radiolabelled compound is usually administered so that positron emissions caused by radioactive decay of the $^{18}F$ isotopes can be detected by imaging equipment, such as positron emission tomographs.

Generally, a dose of the $^{18}F$-labelled substituted 2-aminotetralin is administered to a human such that the radioactive content of the dose is between 1 and 10 millicuries, preferably between 1 and 5 millicuries. The radioactive dosage will generally be determined according to known methods for determining the critical organ dosage in the subject species for the compound used.

Positron emissions are used to form an image and/or series of radiophoto images, usually in cross-section, showing the distribution at equilibrium of the radiolabelled ligands within the body, for example, within the brain. Therefore, it is important to allow a sufficient interval of time between administration of the radiolabelled substrate and commencement of the imaging regime for the radiolabelled ligand to reach an equilibrium distribution within the body. However, in practice it may be more convenient to monitor establishment of equilibrium using the imaging equipment itself.

In the method of detecting schizophrenia in humans and other abnormalities in $D_2$ receptor levels affecting cerebral function, images of the subject brain showing the distribution of the radiolabeled ligand at equilibrium concentrations are compared with images showing the equilibrium distribution of the same radioligand at $D_2$ receptor sites in the brains of other members of the subject species whose level and/or distribution of dopamine $D_2$ receptors is considered normal. Abnormal levels or distribution of $D_2$ receptors in the subject brain will indicate that the subject has at least an increased probability of suffering from schizophrenia or other physiological and/or psychological abnormalities. This will allow appropriate treatment to be initiated. For example, when the level is elevated it is believed that schizophrenia is indicated.

The following examples illustrate the manner in which the invention can be practiced. It is understood, however, that the examples are for the purpose of illustration and the invention is not to be regarded as limited to any of the specific materials or conditions therein.

To prepare the fluorinated dopamine $D_2$ receptor agonists herein the following procedure was used.

EXAMPLE 1

Preparation of 2-[N-3-Fluoropropyl-N-2-(2-thienyl) ethylamino]-5-hydroxytetralin

Step 1

1.6-Dimethoxynaphthalene 1,6-Dimethoxynapthalene was prepared according to the method of Ames, et al., *J. Chem. Soc.*, 1965, 2636, as follows: To a stirred solution of 250 g (1.56 mole) 1,6-dihydroxynapthalene in 1.4 L of 2N sodium hydroxide solution was added 310 mL dimethyl sulfate and this was stirred at 50° C. A further 700 mL of 2N NaOH solution and 170 mL of dimethyl sulfate was added. The solution was stirred and kept at a pH of 10. After refluxing 1 hour and overnight cooling, the aqueous layer was separated from the oil and extracted with dichloromethane. The organic layer was combined with the oil, concentrated, and purified by flash chromatography (Silica; $CH_2Cl_2$) to yield the product (87% yield) as a white solid: m.p. 54°-57° C.; NMR (300 MHz, $CDCl_3$)δ8.15 (1H,d), 7.35(2H,m), 7.12(2H,m), 6.65(1H,m), 3,95(3H,s), 3.85(3H,s).

Step 2

5-Methoxy-2-tetralone

5-Methoxy-2-tetralone was prepared according to the method of Ames et al., *J. Chem. Soc.*. 1965, 2636, as follows: To a boiling solution of 100 g (0.53 mol) of 1,6-dimethoxynapthalene in 1.4 L EtOH was added 90 g (3.91 mol) sodium shavings and the mixture was stirred until all the sodium was dissolved. The reaction was cooled to 0° C., and 457 mL concentrate HCl and 395 mL $H_2O$ was added dropwise and refluxed one hour. The mixture was filtered and the filtrate was concentrated, dissolved in $H_2O$ and extracted with diethyl ether. The organic layer was concentrated and dissolved in 60 mL saturated sodium bisulfite, stirred for 20 min., then filtered. The resulting solid was freed and distilled to give the product (65% yield) as a clear oil: NMR ($CDCl_3$)δ7.2(1H,m), 6.8(2H,m), 3.9(3H,s), 3.6(2H,s), 3.1(2H,m), 2.55(2H,m).

Step 3

2-[N-2(2-Thienyl)ethylamino]-5-methoxytetralin hydrochloride

A solution of 16.7 g (0.095 mol) of 5-methoxy-2-tetralone 14.5 g (0.114 mol), of 2-(2-thienyl)ethylamine, and a catalytic amount of p-toluenesulfonic acid in dry toluene was refluxed under a Dean-Stark trap for 2.5 hours. The mixture was concentrated in vacuo and the residue dissolved in THF and brought to pH 2-3 followed by addition of 5.95 g (0.095 mol) of sodium cyanoborohydride. After additional stirring at room temperature for 2 hours, the mixture was filtered and washed several times with diethyl ether to yield 15.8 g (51%) of the product as a white solid: NMR (free base) ($CDCl_3$):δ7.2-6.6 (6H,m), 3.8(3H,s), 3.1-2.8(7H,m), 2.6-2.5(2H,m), 2.05(1H,m), 1.55(1H,m).

Step 4

2-[N-2-(2-Thienyl)ethylamino]-5-hydroxytetralin

To a solution of 4.95 g (0.015 mol) of the product of Step 3 in dry dichloromethane was added 80 mL of boron tribromide under $N_2$. The mixture was stirred 1 hour at room temperature then poured over $NH_4OH$ and ice. The organic layer was separated and dried over $MgSO_4$, and concentrated to yield 1.0 g of product: NMR ($CDCl_3$)δ7.2-6.6(6H,m), 3.1-2.8(7H,m), 2.7-2.5(2H,m), 2.15(1H,m), 1.65(1H,m).

Step 5

1-Bromo-3-fluoropropane

This compound was prepared in 30% yield according to the method of Hoffman, *J. Org. Chem.*, 1950, 15,81. To a stirred solution of 8.6 g (0.15 mol) potassium fluoride in ethylene glycol of 80°-100° C. was added 20 g (0.1 mol) of 1,3-dibromopropane. The mixture was stirred for 7 hours, cooled, and stirred overnight. After workup and fractional distillation (105°-110° C.), the product was isolated as a clear solution. NMR ($CDCl_3$δ4.62(2H,dt), 3.55(2H,t), 2.25(2H,m).

Step 6

2-[N-3-Fluoropropyl-N-2-(2-thienyl)ethylamino]-5-hydroxytetralin

To a stirred solution of 300 mg (1.10 mmol) of the compound of Step 4, 165 mg (1.10 mmol) of NaI in 10 mL acetonitrile was added. Then 202 mg (1.43 mmol) of 1-bromo-3-fluoropropane was added and the mixture was refluxed overnight. The solution was concentrated in vacuo and the residue was purified by liquid chromatography (Silica, 9:1 pet ether/EtOAc) to yield 90 mg (28%) of product as a colorless oil: NMR ($CDCl_3$)δ7.1-6.5(6H,m), 4.5(2H,dt J=47.25,5.76 Hz), 3.1-2.5(11H,m), 2.1(1H,m,), 1.9-1.5(3H,m).

The free base was converted to the corresponding hydrochloride salt by addition of an ether/HCl solution to give 100 mg of the salt as a white solid: m.p.=105°-109° C. Analytical calculation for $C_{19}H_{25}ClFNOS$: C, 61.69; H,6.81; N,3.79. Found: C,61.63; H,6.86; N,3.63.

EXAMPLE 2

Preparation of $^{18}F$-radiolabelled 2-[N-(3-[$^{18}F$]fluoropropyl)-N-2-(2-thienyl)ethylamino]-5-hydroxytetralin.

$^{18}F$-radiolabeled 2-[N-3-[$^{18}F$]fluoropropyl)-N-2-(2-thienyl)ethylamino]-5-hydroxytetralin is prepared by the reaction of the product of Step 4 with 1-bromo-3-[$^{18}F$]fluoropropane. 1-Bromo-3-[$^{18}F$]fluoropropane is prepared according to the method of Chi, et al., *Int. J. Appl. Radiat. Isot.*, 1986, 37, 1173. Fluorine-18, prepared from [$^{18}$]$H_2$(>95%) by the $^{18}O(p,n)^{18}F$ reaction in a metal cyclotron target, is combined with ñ-tetrabutylammonium hydroxide in a small reaction vial, and dried by azeotropic distillation, using small aliquots of acetonitrile, under a stream of dry nitrogen at 90°–100° C. The dried $^{18}$F-fluoride is resolubilized in acetonitrile, and 3-Bromo-1-[((trifluoromethyl)sulfonyl)oxy]propane (prepared according to the method of Chi, et al., *J. Org. Chem.*, 1987, 52, 658) is added, and the mixture is stirred for several minutes. The product of Step 4 is added, and the mixture is stirred at 120° C. for 30 minutes. The reaction mixture is cooled, diluted with acetonitrile, and passed through a sodium sulfate column. The mixture is purified by HPLC.

EXAMPLE 3

The selectivity of 2-[N-3-fluoropropyl-N-2-(2 thienyl)ethylamine]-5-hydroxytetralin has been investigated using radioligand binding assays to determine the binding affinity at different receptor types, namely $D_1$ and $D_2$ dopamine and α-adrenergic receptor sites.

Membranes derived from bovine striatum (for assaying dopamine receptors) and rat cerebral cortex (for assaying α-adrenergic receptors) were prepared as follows. The tissue was homogenized using a tissue disrupter and centrifuged. The pellet was washed by resuspension and centrifugation. The bovine striatal membranes were incubated at 37° C. and thawed just prior to use.

The radioligands $^3$H-prazosin, H$^3$[((R)-(+)-8 chloro-2, 3, 4, 5-tetrahydro-3-methyl-5-phenyl-H-3-benzazepin-7-ol]($^3$H-SCH23390), and H$^3$[5-hydroxy-2-(N-n-propyl-N-2-[2-thienyl]ethylamino)tetralin] ($^3$H-N-0437) were used to label α-adrenegic, $D_1$-dopamine and $D_2$-dopamine receptors, respectively. Increasing concentrations of 2-[N-3-fluoropropyl-N-2-(2-thienyl)ethylamine]-5-hydroxy-tetralin were used to displace the binding of these radioligands from their respective receptors. Competition binding curves were hand drawn to fit the data, and IC$_{50}$ values were determined graphically. The IC$_{50}$ value indicates the concentration of test drug required to displace from attachment at the receptor site of interst 50 percent of the ligands of known affinity already in attachment there. The results of these binding assays are shown below in Table 1.

TABLE 1

| Receptor Type | IC$_{50}$ Values (nM) |
|---|---|
| D$_1$-dopamine | >10,000 |
| D$_2$-dopamine | 1.03 ± 0.49 |
| α-adrenergic | 5,700 ± 3,000 |

This shows the test substance is selective for D$_2$-dopamine receptors. Moreover, it is more than 5000 times more potent in binding to D$_2$-dopamine receptors than in binding to α-adrenergic receptors, and more than 10,000 fold more selective for D$_2$- than for the D$_1$-dopamine receptors.

It had been thought that fluorine, a highly electronegative atom, could not be incorporated within the unfluorinated ligand without reducing the basicity by which it is believed that affinity for dopamine D$_2$ receptor sites is generated. However, the unexpectedly high affinity of the fluorinated agonist herein proves that incorporation of the fluorine atom does not substantially reduce affinity of the ligand.

While particular embodiments of the invention have been described it will be understood of course that the invention is not limited thereto since many obvious modifications can be made and it is intended to include within this invention any such modifications as will fall within the scope of the appended claims.

Having now described the invention, We claim:

1. A method for detecting dopamine D$_2$ receptor abnormalities in the brain of a mammal, said method comprising (1) administering an amount of a radiolabelled compound sufficient to be detected by a positron emission sensitive brain imaging means, said compound having affinity for said receptors and consisting of an optically active or racemic compound represented by the general formula:

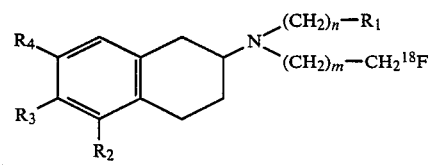

wherein R$_1$ is selected from the group consisting of organic radicals methyl, substituted or unsubstituted phenyls, pyridyl, hydroxyphenyl,

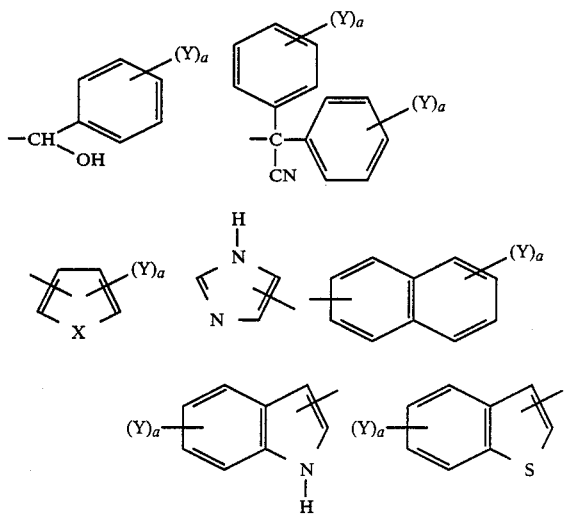

X is oxygen or sulfur, Y is selected from the group consisting of hydroxy, nitro, cyano, azido, amino, acylamino, carboxyamido, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from zero to 3, R$_2$, R$_3$ and R$_4$ are each selected from the group consisting of H and OA, A is H or is selected from the group consisting of hydrocarbyl radicals,

and

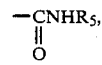

$R_5$ is selected from the group consisting of hydrocarbyl radicals; m is an integer between 0 and 2; n is an integer between 1 and 3; with the provision that at least one of $R_2$, $R_3$ and $R_4$ is H, that at least one of $R_2$, $R_3$ and $R_4$ is not H, and that $R_2$ and $R_4$ are not both OA, except that when $R_1$ is meta-hydroxyphenyl, phenyl, or 2-thienyl, the compound is optically active and pharmaceutically acceptable salts thereof.

(2) forming at least one image showing the distribution of the radiolabelled compound within the brain of the human or other mammal using a positron emission-sensitive means for brain imaging; and (3) determining normality of the concentrations or distribution by comparing the image with an image showing the normal concentrations and distribution of the receptors in the brains of humans or mammals of the same species.

2. The method of claim 1 wherein the compound is the negative isomer of 2-[N-(3-[$^{18}$F]fluoropropyl-N-2-(2-thienyl)ethylamino]-5-hydroxytetralin.

3. The method of claim 1 wherein the positron emission sensitive means forms a tomographic image.

4. The method of claim 3 wherein the means is a positron emission tomograph.

5. The method of claim 4 wherein said abnormality is schizophrenia.

6. The method of claim 3 wherein $R_4$ is H and $R_2$ and $R_3$ are OH or $R_2$ is H and $R_3$ and $R_4$ are OH.

7. The method of claim 3 wherein $R_3$ and $R_4$ are H and $R_2$ is OH.

8. The method of claim 3 wherein $R_2$ and $R_3$ are H and $R_4$ is OH and wherein n is 2.

9. The method of claim 3 wherein $R_3$ and $R_4$ is H and $R_2$ is OH, n is 2 and X is 0.

10. A method for detecting abnormal concentrations and distribution of dopamine $D_2$ receptors in a human or other mammal, said method comprising:

(1) administering to a human or other mammal an amount of a $^{18}$F-radiolabelled compound sufficient to be detected by a positron emission-sensitive means for imaging, said compound having affinity for said receptors selected from the group consisting of optically active or racemic compounds represented by the general formula:

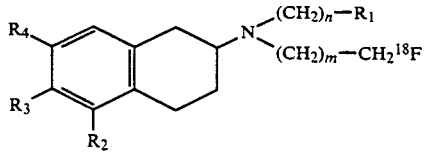

wherein $R_1$ is selected from the group consisting of organic radicals methyl, substituted or unsubstituted phenyls, pyridyl, hydroxyphenyl,

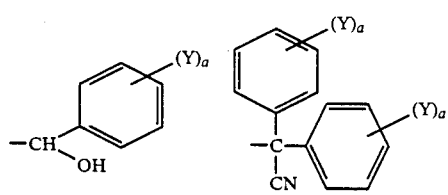

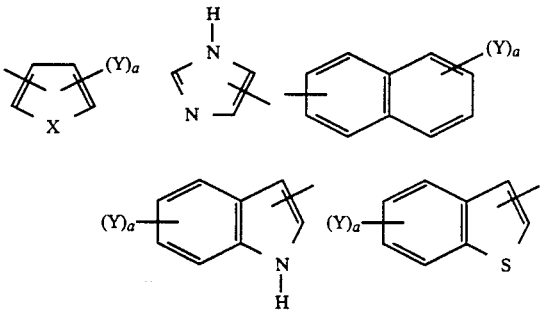

X is oxygen or sulfur, Y is selected from the group consisting of hydroxy, nitro, cyano, azido, amino, acylamino, carboxyamide, trifluoromethyl, sulfate, sulfonamido, halogen, hydrocarbyl and hetero atom-substituted hydrocarbyl radicals, wherein said heteroatoms are selected from the group consisting of halogen, nitrogen, oxygen, sulfur and phosphorus and said hydrocarbyl radicals comprise from 1 to 12 carbon atoms, and a is an integer of from zero to 3, $R_2$, $R_3$ and $R_4$ are each selected from the group consisting of H and OA, A is H or is selected from the group consisting of hydrocarbyl radicals,

and

$R_5$ is selected from the group consisting of hydrocarbyl radicals; m is an integer between zero and 2; n is an integer between 1 and 3; with the provision that at least one of $R_2$, $R_3$ and $R_4$ is H, that at least one of $R_2$, $R_3$ and $R_4$ is not H, and that $R_2$ and $R_4$ are not both OA, except that when $R_1$ is meta-hydroxyphenyl, phenyl, or 2-thienyl, the compound is optically active and pharmaceutically acceptable salts thereof;

(2) forming at least one image showing the distribution of the radiolabelled compound within the human or other mammal using a positron emission-sensitive means for imaging; and (3) determining normality of the concentrations or distribution by comparing the image with an image showing the normal concentrations and distribution of the receptors in humans or mammals of the same species.

11. The method of claim 1 wherein $R_4$ is H and $R_2$ and $R_3$ is OH.

12. The method of claim 1 wherein $R_3$ and $R_4$ are H and $R_2$ is OH.

13. The method of claim 1 wherein $R_2$ and $R_3$ are H and $R_4$ is OH and wherein n is 2.

14. The method of claim 1 wherein $R_3$ and $R_4$ is H and $R_2$ is OH, n is 2, and X is 0.

15. The method of claim 1 wherein the compound is the negative isomer of 2-[N-(3-[$^{18}$F]fluoropropyl)-N-2-(2-thienyl)ethylamino]-5-hydroxytetralin.

16. The method of claim 1 wherein the positron emission sensitive means forms a tomographic image.

17. The method of claim 2 wherein the means is a positron emission tomograph.

18. The method of claim 2 wherein the subject is human, the receptors are located in the brain and said abnormality is schizophrenia.

19. The method of claim 2 wherein the subject is human, the receptors, are located in the brain and said abnormality is Parkinson's disease.

20. The method of claim 2 wherein the subject is human, the receptors are located in the drain and said abnormality is Huntington's disease.

21. The method of claim 2 wherein said abnormality is Parkinson's disease.

22. The method of claim 2 wherein said abnormality is Huntington's disease.

* * * * *